United States Patent [19]

Plueddemann

[11] Patent Number: 5,041,593
[45] Date of Patent: Aug. 20, 1991

[54] METHOD FOR PREPARATION OF SILYL FUNCTIONAL FUMARATES

[75] Inventor: Edwin P. Plueddemann, Midland County, Mich.

[73] Assignee: Dow Corning Corporation, Midland, Mich.

[21] Appl. No.: 381,916

[22] Filed: Jul. 19, 1989

[51] Int. Cl.$^5$ .............................. C07F 7/08; C07F 7/18
[52] U.S. Cl. .................................................... 556/440
[58] Field of Search ......................................... 556/440

[56] References Cited

U.S. PATENT DOCUMENTS

| | | | |
|---|---|---|---|
| 3,179,612 | 4/1965 | Plueddemann | 260/29.2 |
| 3,759,968 | 9/1973 | Berger et al. | 556/440 |
| 3,773,817 | 11/1973 | Berger et al. | 556/440 |
| 3,941,741 | 3/1976 | De Zuba et al. | 556/440 |
| 4,093,641 | 6/1978 | Plueddemann | 556/440 |
| 4,273,698 | 6/1981 | Smith, Jr. et al. | 556/440 |
| 4,281,145 | 7/1981 | Mitchell | 556/440 |
| 4,331,797 | 5/1982 | Martin | 556/440 X |
| 4,910,232 | 3/1990 | Arai | 556/440 X |

Primary Examiner—Paul F. Shaver
Attorney, Agent, or Firm—Sharon K. Severance

[57] ABSTRACT

Silyl-functional fumarates are formed through the reaction of a methyl ester of a maleate with a chloroalkyl silane or disiloxane in the presence of an amine or phosphine catalyst. These materials are useful as adhesion promoters for polyolefins.

9 Claims, No Drawings

METHOD FOR PREPARATION OF SILYL FUNCTIONAL FUMARATES

This invention relates to silyl-functional fumarates and a method for their preparation.

BACKGROUND OF THE INVENTION

Silyl-functional fumarates as well as maleates are well known in the art. There are many literature sources describing their preparation and uses.

The most common preparation of these materials is to react, in the presence of a catalyst, a maleate or fumarate containing an unsaturated hydrocarbon on the end or ends of the molecule with a hydrogen halogensilane or alkoxysilane. These reactions are often difficult and ineffective. The handling of toxic chemicals is required in some of them, platinum catalysts are used, and the raw materials may not be readily available and complex to produce.

Mitchell, U.S. Pat. No. 4,281,145 produces silyl functional maleates and fumarates by reacting a hydrogen chlorosilane with an olefinic maleate or fumarate in the presence of platinum. The resulting silyl-functional maleate or fumarate is then reacted with an alcohol to provide the desired alkoxy functionality. This process requires the difficult addition reaction step and the use of a platinum catalyst, however, it has eliminated the handling of toxic starting materials. It is also preferred that in Mitchell the addition reaction be carried out in the presence of an organic solvent.

Berger et. al., U.S. Pat. No. 3,759,968 is a less efficient method similar to that taught by Mitchell. Berger et al provides further detail to show the complexity of producing the starting materials necessary for the disclosed method.

Berger et. al., U.S. Pat. No. 3,773,817 teaches a method in which an hydrogenalkoxysilane is reacted in the presence of platinum with an olefinic maleate to produce the silyl-functional maleate. However the desired starting hydrogenalkoxysilane is hydrogentrimethoxysilane which is known in the art to be highly toxic. Also this reaction results in low yields of product.

The reaction mechanisms taught by prior art make it impossible and unobvious to produce silyl-functional fumarates or maleates in which there is less than 2 carbons joining the silicon molecule to the fumarate or maleate joining the silicon molecule to the fumarate or maleate group. The is due to the necessity of having a C=C bond on the maleate or fumarate for addition to the silane.

It is an object of this invention to present a method for production of silyl-functional fumarates that does not require addition across a double bond, the use of platinum or the handling of toxic starting materials.

It is further an object to present novel silyl-functional fumarates that are prepared by this method.

It is further an object of this invention to provide a method of adhering polyolefins to various substrates using silyl-functional fumarates.

THE INVENTION

This invention relates to silyl-functional fumarates of the formula

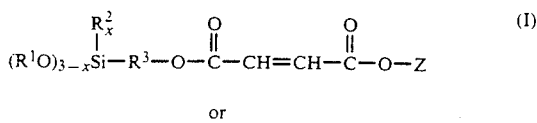

or

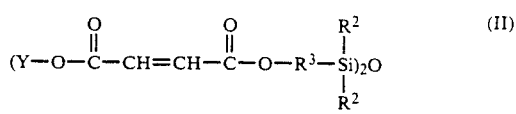

wherein each $R^1$ is independently selected from an alkyl group having 1 to 4 carbons, each $R^2$ is independently selected from $R^1$ and phenyl, each $R^3$ is independently selected from a straight or branched chain alkylene group having 1 to 10 carbons, each Z is independently selected from the hydrogen atom, $R^1$ and $-R^3SiR^2_x(OR^1)_{3-x}$, each Y is independently selected from the hydrogen atom and $R^1$ and x has a value of 0 to 3.

$R^1$ can be further exemplified by alkyls such as methyl, ethyl, butyl, propyl, and iso-propyl. $R^2$ can be further exemplified by alkyls such as methyl and ethyl, or aryls such as phenyl. $R^3$ can be further exemplified by methylene, ethylene, propylene, butylene, iso-butylene, hexylene, phenylene.

The silyl-functional fumarates of this invention are produced by the reaction of a methyl ester of a maleate with a haloalkyl alkoxysilane in the presence of an amine or phosphine while generating methyl chloride gas as a by-product. It is also possible to use haloalkyl or haloaryl disiloxanes to produce polyester siloxane-fumarates by the method of this invention.

Haloalkyl or haloaryl alkoxysilanes applicable in this invention are of the formula:

where $R^1$, $R^2$, and $R^3$ are as previously described and X is a halogen. The preferred structure is when $R^1$ is methyl, $R^2$ is methyl, $R^3$ is methylene, ethylene, propylene, iso-butylene and X is chlorine.

Haloalkyl or haloaryl disiloxanes applicable in this invention are of the formula

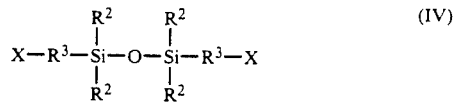

where $R^2$, $R^3$, and X are as previously described. It is preferable that every $R^2$ on the molecule be identical however this is not always necessary. The preferred structure of the molecule is where $R^2$ is methyl, $R^3$ is methylene, ethylene, propylene, iso-butylene and X is chlorine.

Maleates useful in this invention have the general formula

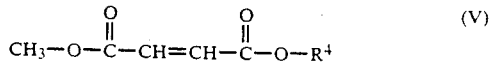

where $R^4$ is selected from the hydrogen atom and an alkyl group having 1 to 4 carbons. The preferred structure is when $R^4$ is selected from the hydrogen atom or the methyl group.

The silyl-functional fumarates are formed because the starting maleate undergoes isomerization during the reaction. The maleate may also isomerize prior to the reaction forming a fumarate. The fumarate is not very reactive in the method of this invention and it tends to sublime in the process equipment causing plugging problems. This initial isomerization into the fumarate can be controlled by using an excess of the silane and the addition of trace amounts of basic materials.

The method for making the silyl-functional fumarates comprises i) reacting an excess of III or IV with V at temperatures at which the reactants reflux in the presence of an amine or phosphine catalyst for a period of time sufficient to remove all of the alkyl chloride, and then ii) subjecting the resulting reaction mixture to a reduced pressure and elevated temperature to remove low boilers and the excess III or IV. A basic material such as $Na_2CO_3$ may be added during the reaction step (i) to prevent V from isomerizing before the reaction has occurred. The strip step (ii) is not necessary in certain applications of the product in which the excess III or IV will not hinder the performance of the material.

The haloalkyl alkoxysilane or disiloxane is used in an excess from 5 to 30 percent based on the theoretical weight of alkoxy or disiloxane required to form the product.

Examples of amine catalysts applicable in this invention include tertiary amines such as tetramethylguanadine, benzyl dimethylamine, triethylamine, and others. If secondary or primary amines are used they must be of the type so that when they react with the haloalkyl disiloxanes they form quaternary salts.

Examples of phosphine catalysts applicable in this invention include tributylphosphine, dibutylmonomethyl-phosphine and others.

The amount of catalyst needed varies but is usually from 0.1 to 5 percent based on the total weight of the reaction mixture.

The basic material may be added at the start of the reaction process. Quantities up to 10 percent based on the amount of maleate used may be added. The basic material may be filtered off at the end of the strip (ii) if it is used during the process of making the silyl-functional fumarate.

Other materials such as hydroquinone monomethyl ether and possible other phenolic inhibitors can be added to stabilize the fumarate double bond in the resulting product so that the product may be distilled or processed otherwise at high temperatures without polymerizing the fumarate double bond.

It is feasible to form a bis silyl-functional fumarate by using 2 moles (plus the desired excess) of the alkoxysilane for every mole of the maleate (V) where $R^4$ is an alkyl group, preferably methyl. It is also possible to stop the reaction or use less than 2 moles but greater than 1 mole to form a mixture of bis- and mono-substituted silyl-functional fumarates.

The silyl-functional fumarates of this invention are useful as coupling agents for organic polyolefins. The polyolefins may be coupled to substrates such as glass, ceramic, metal or metal oxides. Examples of preferred polyolefins are homopolymers of ethylene and propylene and various copolymers of ethylene.

A method for coupling the polyolefins to the substrates comprises (i) mixing silyl-functional fumarates of this invention with an alcohol,
(ii) applying the mixture of (i) to the substrate
(iii) drying coated substrate of (ii),
(iv) applying the polyolefin to dried substrate and,
(v) melting the polyolefin in contact with the substrate.

The silyl-functional fumarates of this invention are diluted in a solvent so that they comprise 5 to 90 percent of the total solution and then applied them to the substrate by methods such as wiping, flowing, dipping, spraying and others. The silyl-functional fumarate is allowed to dry by removal of the solvent on the surface of the substrate. Methods for evaporation include air drying, the application of heat and others. The polyolefin may then be melted or fused at temperatures of 200 to 300 degrees Celsius.

The solvents used in diluting the silyl-functional fumarate are alcohols. These may be further exemplified by the alcohols such as methanol, ethanol, or propanol, isopropanol, butanol and others. The amount of solvent present should comprise from about 10 percent to 95 percent by weight of the total solution. Substrates applicable for the application of the fumarates are selected essentially from glass, ceramic, metal or metal oxides.

So that those skilled in the art can understand and appreciate the invention taught herein, the following examples are presented, being it understood that these examples should not be used to limit the scope of this invention over the limitations found in the claims attached hereto.

EXAMPLE 1

72 grams of dimethylmaleate (0.5 moles) and 200 grams chloropropyltrimethoxysilane (1 mole) and 3 grams benzyl dimethylamine were heated with stirring to a reflux temperature of 180 degrees Celsius while measuring the methyl chloride evolution by collecting it in a 500 ml graduated glass cylinder inverted in a pan of water. Gas evolution was very slow reaching a maximum of about 40 ml/min. An additional 4 grams of tetramethylguanadine catalyst was added which within a few minutes caused the reaction to accelerate generating up to 650 ml/min. of methyl chloride. Reaction finally tapered to less than 50 ml/min. methyl chloride at 200 degrees Celsius pot temperature which was taken as the end of the reaction. The material was distilled under vacuum resulting in recovery of 16 grams of chloropropyltrimethoxy- silane b 70-80 degrees, 0.5 torr; 30 grams of the monosubstituted fumarate ester b 140-150 degrees, 0.5 torr; and 56 grams of the bis substituted ester b 200-205 degrees, 0.5 torr, $n_D$ 1.4448, $d_4$ 1.118, and a large tarry residue.

EXAMPLE 2

36 grams of dimethylmaleate (0.25 moles), 120 grams of chloropropyltrimethoxysilane (0.60 moles), 4 grams of tetramethylguanadine and 3 grams of hydroquinone monomethyl ether was warmed to 184 degrees Celsius with a maximum rate of methyl chloride evolution, measured as in Example 1, of 500 ml/min. at 175 degrees Celsius. The reaction product was a dark viscous oil.

EXAMPLE 3

36 grams of dimethylmaleate (0.25 moles), 120 grams of chloropropyltrimethoxysilane (0.60 moles), 4 grams of tetramethylguanadine, 3 grams of hydroquinone monomethyl ether and 3 grams of anhydrous Na₂CO₃ was warmed to 184 degrees Celsius with a maximum rate of methyl chloride evolution of 180 ml/min. at 175 degrees Celsius. The cooled product was filtered to obtain a product that was lighter and less viscous than in example 2.

EXAMPLE 4

Sample A: Distilled mono-substituted fumarate ester prepared in Example 1.

Sample B: Distilled bis-substituted fumarate ester prepared in Example 1.

Sample C: Unstripped reaction mixture prepared in Example 3.

Samples A, B and C were diluted to 20 percent in methanol. They were wiped by hand using a saturated cloth on clear glass microscope slides and aluminum panels and allowed to air dry. High molecular weight polyethylene was pressed against the primed substrate surface at a temperature of 250 degrees Celsius. Initial adhesion of the polyethylene to the substrate was greater than 30 N/cm peel strength.

The substrates were then submerged in boiling water for a period of 24 hours or until peel strength differences were observed. Although there appeared to be some loss of adhesion at the edges the overall peel strength remained above 30 N/cm. Results are given in Table I.

EXAMPLE 4

For comparative purposes the following materials were diluted and applied in the same manner as described previously. Both are known in the art as coupling agents for polyolefins.

Sample D: (MeO)₃Si(CH₂)₃NH₂CH₂Ch₂N(H)CH₂PhCH₂=CH₂ where Ph stands for phenyl and Me is methyl.

Sample E:

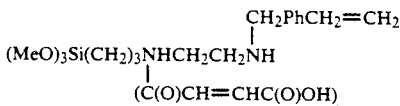

Both samples failed before the 24 hour test period had been completed. Results are given in Table I.

TABLE I

| Sample | Glass Substrate Boil Time | | | | Aluminum Substrate Boil Time | | | |
|---|---|---|---|---|---|---|---|---|
| | 2 hr. | 4 hr. | 8 hr. | 24 hr. | 2 hr. | 4 hr. | 8 hr. | 24 hr. |
| D | C | 9.6 | — | — | C | 13.5 | — | — |
| E | C | 11.6 | — | — | C | 4.6 | — | — |
| A | C | C | C¹ | C¹ | C | C | C¹ | C¹ |
| B | C | C | C | C | C | C | C | C |
| C | C | C | C¹ | C¹ | C | C | C¹ | C¹ |

C = cannot peel at 30 N/cm
C¹ = loose areas on edges, overall adhesion still >30 N/cm

What is claimed is:

1. A process for making silyl-functional fumarates which comprises
   (I) reacting a silicon-containing precursor selected from the group consisting essentially of
   (i) silanes of the general formula

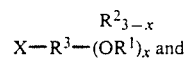

and (ii) siloxanes of the general formula

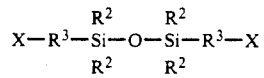

with a maleate having the general formula of

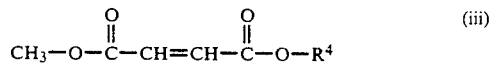 (iii)

in the presence of amines or phosphines capable of forming -onimum compounds with the reactants;
   said reaction being conducted at a temperature sufficient to maintain reflux;
   said reaction being conducted for a time sufficient to remove any alkyl chloride formed;
   (II) subjecting the resulting reaction mixture to reduced pressure and elevated temperatures to remove any undesired low boiling materials, and
   (III) recovering any silyl-functional fumarates formed thereby, wherein each $R^1$ is independently selected from an alkyl group having 1 to 4 carbons;
   each $R^2$ is independently selected from $R^1$ and phenyl;
   each $R^3$ is independently selected from alkylene groups having 1 to 10 carbons;
   $R^4$ is selected from $R^1$ and the hydrogen atom; X is a halogen atom and, x has a value of 0 to 3.

2. A process as claimed in claim 1 where an amine is present during the reaction, the silicon-containing precursor is (i), $R^1$ is methyl, $R^2$ is methyl and X is chlorine.

3. A process as claimed in claim 2 wherein the amine is tetramethylguanadine.

4. A process as claimed in claim 1 wherein a silane is used and $R^1$ is methyl, $R^2$ is methyl, $R^3$ is methylene, and X is chlorine.

5. A process as claimed in claim 1 wherein a silane is used and R1 is methyl, $R^2$ is methyl, $R^3$ is —CH₂CH₂CH₂— and X is chlorine.

6. A process as claimed in claim 1 wherein a siloxane is used and $R^2$ is methyl, $R^3$ is methylene, and X is chlorine.

7. A process as claimed in claim 1 wherein a siloxane is used and $R^2$ is methyl, and X is chlorine.

8. A process as claimed in claim 1 wherein a siloxane is used and $R^2$ is methylene, $R^3$ is —CH₂CH₂CH₂— and X is chlorine.

9. A process as claimed in claim 1 wherein the maleate has the formula

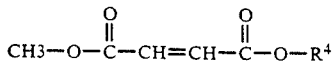

and $R^4$ is methyl.

* * * * *